(12) United States Patent
Nakae et al.

(10) Patent No.: US 7,045,047 B2
(45) Date of Patent: May 16, 2006

(54) GAS SENSOR ELEMENT

(75) Inventors: Makoto Nakae, Nagoya (JP); Susumu Naito, Kariya (JP); Namitsugu Fujii, Yokkaichi (JP); Hiromi Sano, Nagoya (JP); Tomio Sugiyama, Nagoya (JP); Kazuya Nakagawa, Kariya (JP)

(73) Assignee: Denso Corporation, (JP)

( * ) Notice: Subject to any disclaimer, the term of this patent is extended or adjusted under 35 U.S.C. 154(b) by 0 days.

(21) Appl. No.: 10/323,918

(22) Filed: Dec. 20, 2002

(65) Prior Publication Data

US 2003/0116448 A1 Jun. 26, 2003

(30) Foreign Application Priority Data

Dec. 20, 2001 (JP) ............... 2001-387705
Oct. 22, 2002 (JP) ............... 2002-307491

(51) Int. Cl.
*G01N 27/41* (2006.01)

(52) U.S. Cl. ............... 204/425; 204/402; 204/427

(58) Field of Classification Search ........ 204/421–429, 204/902
See application file for complete search history.

(56) References Cited

U.S. PATENT DOCUMENTS

| | | | | |
|---|---|---|---|---|
| 4,169,777 A | * | 10/1979 | Young et al. | |
| 5,174,885 A | * | 12/1992 | Hayakawa et al. | ......... 204/425 |
| 5,419,828 A | | 5/1995 | Nakano et al. | |
| 5,433,830 A | | 7/1995 | Kawai et al. | |
| 6,007,697 A | * | 12/1999 | Yagi et al. | ................... 205/788 |
| 6,179,989 B1 | * | 1/2001 | Kennard et al. | |
| 6,295,862 B1 | * | 10/2001 | Kurokawa et al. | ......... 73/31.05 |
| 6,332,965 B1 | | 12/2001 | Sugiyama et al. | |
| 6,524,467 B1 | * | 2/2003 | Nakagawa et al. | |
| 6,562,212 B1 | * | 5/2003 | Katafuchi et al. | ........... 204/427 |

FOREIGN PATENT DOCUMENTS

| | | |
|---|---|---|
| JP | 5-18938 | 1/1993 |
| JP | 6-265522 | 9/1994 |
| JP | 7-120429 | 5/1995 |
| JP | 11-72477 | 3/1999 |
| JP | 2002-82091 | 3/2002 |

OTHER PUBLICATIONS

U.S. Appl. No. 09/879,070, filed Jun. 13, 2001 (corres. to JP2002-82091).

* cited by examiner

*Primary Examiner*—Kaj K. Olsen
(74) *Attorney, Agent, or Firm*—Nixon & Vanderhye PC

(57) ABSTRACT

A gas sensor element which may be employed in measuring the concentration of gas such $O_2$, NOx, or CO. The gas sensor element consists of an electrochemical cell made up of a solid electrolyte body formed by a partially stabilized zirconia and a pair of electrodes disposed on the solid electrolyte body. The electrochemical cell is subjected to an aging treatment in which the dc current is applied to the electrodes at a given voltage to enhance the activation of the electrochemical cell.

13 Claims, 12 Drawing Sheets

IN THE AIR

OXYGEN CON. 0.1%

GAS SENSOR ELEMENT

BACKGROUND OF THE INVENTION

1. Technical Field of the Invention

The present invention relates generally to a quickly activatable structure of a gas sensor element which may be built in a gas sensor employed in an air-fuel ratio control system for automotive vehicles for measuring the concentration of gas such $O_2$, NOx, or CO, and a production and a reconditioning method thereof.

2. Background Art

In order to operate a three-way catalyst effectively for converting air pollutants contained in exhaust emissions of automotive engines into harmless products, it is essential to control burning of the engine so as to keep an air-fuel ratio of a mixture within a combustion chamber of the engine within a limited range.

Such air-fuel ratio control typically employs a gas sensor designed to measure the concentration of oxygen ($O_2$) or an unburned gas contained in exhaust emissions of the engine. A gas sensor of such a type is equipped with a gas sensor element having an electrochemical cell made up of a solid electrolyte body and a pair of electrodes disposed on the solid electrolyte body. The electrochemical cell works as an oxygen sensor cell which measures the concentration of $O_2$ or an unburned gas within the exhaust emissions. The air-fuel ratio is determined using an output of the gas sensor and used in controlling the burning of the engine.

For example, U.S. Pat. No. 6,332,965 B1 discloses a gas sensor element of the above described type.

Usually, it is impossible to determine the air-fuel ratio until the temperature of the gas sensor element reaches an activation temperature thereof. It is, therefore, difficult to perform the air-fuel ratio control immediately after startup of the engine. In most cases, the air-fuel ratio control is initiated after the temperature of the gas sensor element reaches the activation temperature.

Specifically, conventional air-fuel ratio control systems have difficulty in controlling the air-fuel ratio correctly until the temperature of the gas sensor element reaches the activation temperature thereof after startup of the engine, which may result in a difficulty in operating the three-way catalyst effectively, so that exhaust gasses containing a high concentration of pollutant are discharged directly to the air.

In recent years, the air-fuel ratio control is sought to be initiated immediately after startup of the engine in order to reduce the concentration of pollutant contained in exhaust gasses of the engine greatly. This requires quick activation of the gas sensor element for measuring the concentration of oxygen correctly immediately after startup of the engine.

In a case where the gas sensor element is used in an exhaust pipe of automotive engines, the gas sensor element usually undergoes a thermal load cyclically over a wide temperature range from room temperature to temperature of exhaust gasses. This results in an increase in electrical resistance of the gas sensor element, thus causing the activation temperature of the gas sensor element to be increased undesirably, which leads to a difficulty in activating the gas sensor element quickly immediately after startup of the engine.

SUMMARY OF THE INVENTION

It is therefore a principal object of the present invention to avoid the disadvantages of the prior art.

It is another object of the present invention to provide a gas sensor element capable of being activated quickly and a production and a reconditioning method thereof.

According to one aspect of the invention, there is provided a production method of a gas sensor element which may be built in a gas sensor for measuring the concentration of gas such $O_2$, NOx, or CO used in an air-fuel ratio control system of automotive vehicles. The production method comprises the steps of: (a) a preparing a gas sensor element including at least one electrochemical cell made up of a solid electrolyte body formed by a partially stabilized zirconia and a pair of electrodes disposed on the solid electrolyte body; and (b) subjecting the electrochemical cell of the gas sensor to an aging treatment in which a dc current is applied to the electrodes. The voltage V of the dc current used in the aging treatment is given by a relation of $V_2 \leq V \leq 2 V_2$ where $V_2$ is a maximum voltage within a limiting current range of the electrochemical cell.

FIG. 6 shows a relation between the voltage applied to the electrochemical cell and a resulting current flowing therethrough. This voltage-current characteristic has three ranges A, B, and C. The range A is between 0 to $V_1$ where the current increases with an increase in the voltage. The range B is between $V_1$ and $V_2$ where the voltage increases, but the current hardly changes. The range C is higher than $V_2$. The current flowing within the range B is generally referred to as a limiting current. The range B is referred to as the limiting current range.

Within the limiting current range, an oxygen ion current produced by ionization of $O_2$ on the surface of the electrode is balanced with the current produced by application of the voltage to the electrochemical cell. When the voltage applied to the electrochemical cell increases and falls within the range C, it will cause the zirconia of the solid electrolyte body to be reduced, thereby resulting in a change in crystalline structure of the solid electrolyte body. This change serves to improve the conductivity of the oxygen ions, thereby resulting in a decrease in activation temperature at which the electrochemical cell is activated.

The decrease in activation temperature is also achieved by applying the dc current to the electrochemical cell to remove the oxygen ions joined to the electrodes, thereby enhancing the activation of the electrodes.

Use of the dc current in the aging treatment facilitates activation of the electrochemical cell and the electrodes as compared with the ac current. The ac current varies in direction of flow thereof. It is, thus, difficult to have the current to flow within the above described voltage range.

The aging treatment is achieved by connecting one of the electrodes to a positive terminal and the other to a negative terminal of a dc power supply. The same effect is provided, as indicated by D and E in FIG. 7, regardless of a direction of flow of the dc current. Note that the current within the range E is the limiting current depending upon a diffusion resistance of an air chamber (i.e., the air chamber 120 as illustrated in, for example, FIGS. 2 and 3).

However, in order to decrease the activation temperature of the electrochemical cell greatly, it is preferable to apply the voltage V across the electrodes so that oxygen ions flow from one of the electrodes exposed to a gas to be measured by the gas sensor element to the other electrode exposed to a reference gas. The aging treatment causes oxygen to be ionized, so that the oxygen ion current flows from the electrode exposed to the measurement gas to the other electrode. The oxygen ions are, thus, removed from the electrode exposed to the measurement gas, thereby increasing the activation of the electrode greatly.

When the concentration of oxygen is measured by the gas sensor element, the ionization of oxygen is taken placed on the electrode exposed to the measurement gas. Increasing the activation of the electrode will result in a decrease in activation temperature thereof, thereby facilitating the activation of the gas sensor element.

In the preferred mode of the invention, at least one of the electrodes is formed by a cermet. For example, the electrode is made by coating the solid electrolyte body with paste of an organic substance or paste including an organic substance and some additive and baking it. The additive may be identical in material with the solid electrolyte body, thereby resulting in a firm joint of the electrode to the solid electrolyte body. However, drawbacks are encountered in that the grain size of the material of and the thickness of the electrode are greater than those of a chemically-plated electrode, and oxygen is joined to the electrode during the baking which results in a decrease in activation of the electrode. The aging treatment of this invention works to enhance the activation of the electrode even if it is made of the cermet.

The aging treatment is performed on the electrochemical cell in an atmosphere where a concentration of oxygen is lower than that of the air.

According to the second aspect of the invention, there is provided a gas sensor element which comprises: (a) at least one electrochemical cell including a solid electrolyte body made of a partially stabilized zirconia; (b) a pair of electrodes disposed on the solid electrolyte body; and (c) a discolored portion formed in the solid electrolyte body between the electrodes.

The zirconia of the solid electrolyte body is capable of being reduced. The discolored portion is formed by the reduction of the zirconia and has a conductivity higher than that of a remaining portion of the solid electrolyte body, thus resulting in a decreased activation temperature of the discolored portion.

According to the third aspect of the invention, there is provided a gas sensor element which comprises: (a) at least one electrochemical cell including a solid electrolyte body made of a partially stabilized zirconia; and (b) a pair of electrodes disposed on the solid electrolyte body. The electrochemical cell works to produce a limiting current within a temperature range of 700° C. to 800° C. in the air regardless of a voltage applied to the electrodes.

Specifically, it is possible to measure the limiting current flowing through the electrochemical cell between 700° C. and 800° C. without changing the voltage applied to the electrochemical cell. This enables the concentration of oxygen contained within exhaust gasses of an internal combustion engine to be measured within a short period of time after startup of the engine.

In the preferred mode of the invention, if a value of the limiting current at 700° C. in the air is defined as $I_{700}$, and a value of the limiting current at 900° C. in the air is defined as $I_{900}$, a relation of $0.8 \times I_{900} \leq I_{700} \leq 1.2 \times I_{900}$.

According to the fourth aspect of the invention, there is provided a reconditioning method of a gas sensor element which includes at least one electrochemical cell made up of a solid electrolyte body made of a partially stabilized zirconia and a pair of electrodes disposed on the solid electrolyte body and which is installed in an exhaust pipe of an internal combustion engine. The reconditioning method is accomplished by applying a dc current to the electrodes of the electrochemical cell at a given voltage V to recondition the electrochemical cell so as to keep a temperature of activation of the electrochemical cell at a desired value. The voltage V is given by a relation of $V_2 \leq V \leq 2V_2$ where $V_2$ is a maximum voltage within a limiting current range of the electrochemical cell.

Usually, when the vehicle is parked, the temperature of the exhaust pipe is substantially identical with an ambient temperature of the vehicle, while it reaches approximately 1000° C. when the vehicle is running and discharging hot exhaust gasses. The gas sensor elements installed in the exhaust pipe is, thus, subjected to a thermal load cyclically within a range of −20° C. to 1000° C., which leads to a decrease in activation of the electrochemical cell. This decrease results in an increase in the activation temperature of the gas sensor element. The reconditioning method of this invention serves to decrease the activation temperature to a desired value.

In the preferred mode of the invention, supply of the dc current to the electrochemical cell is performed during a time when the internal combustion engine is operating and discharging exhaust gasses to the exhaust pipe.

One of the electrodes works as a measurement gas electrode exposed to a gas to be measured by the gas sensor element. The other electrode works as a reference gas electrode exposed to a reference gas. The voltage V is applied across the measurement gas electrode and the reference gas electrode so that oxygen ions may flow from the measurement gas electrode to the reference gas electrode.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
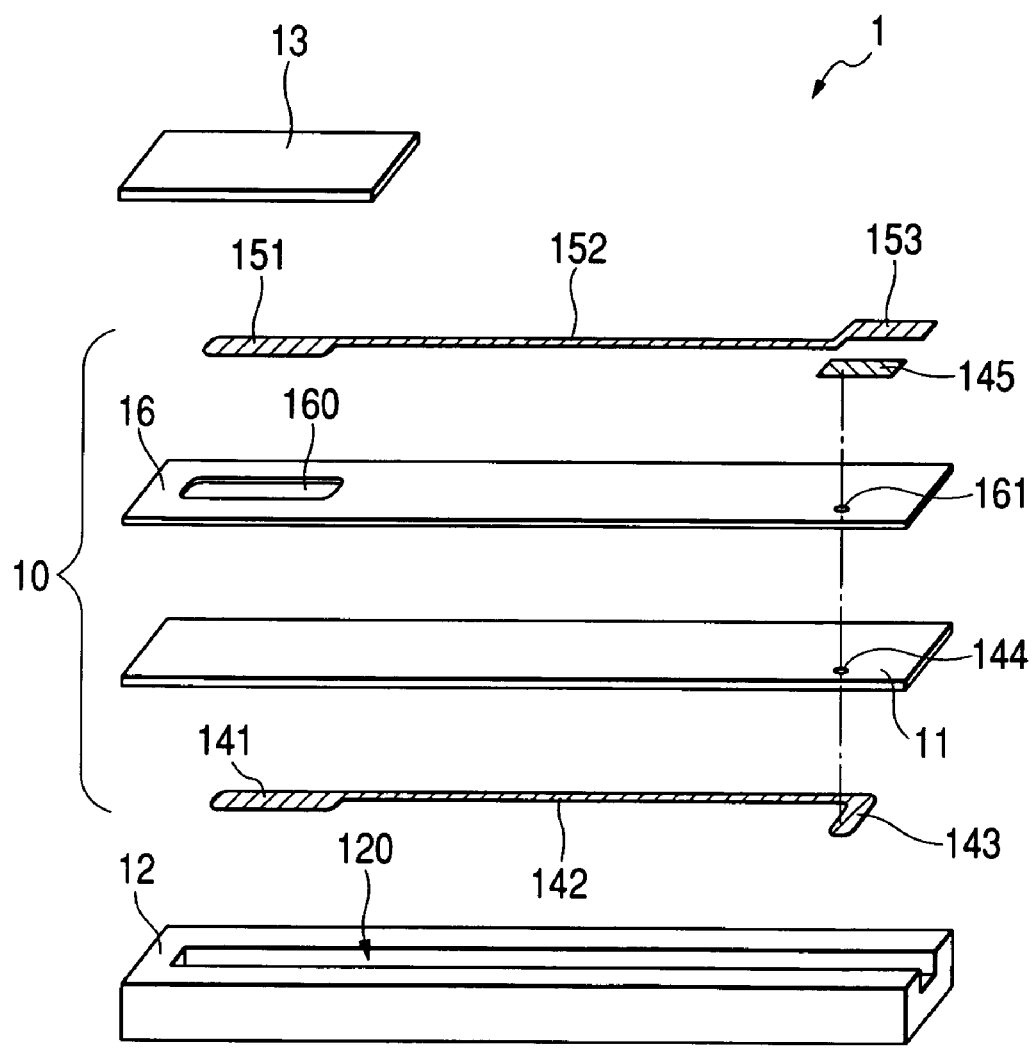
FIG. 1 is an exploded perspective view which shows a gas sensor element according to the first embodiment of the invention.
Figure 1:
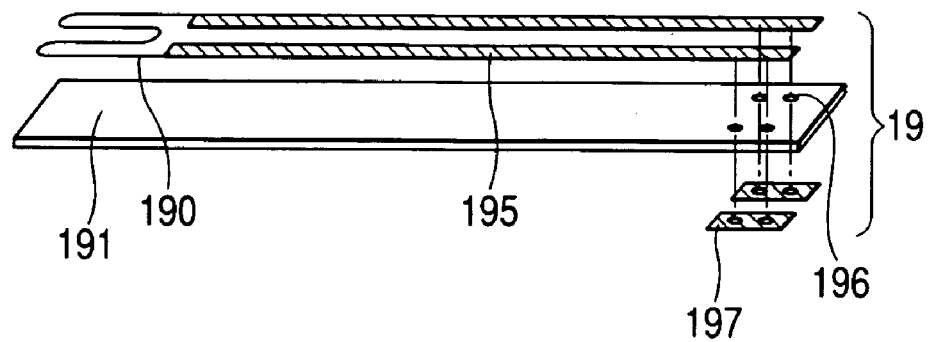
Figure 2:
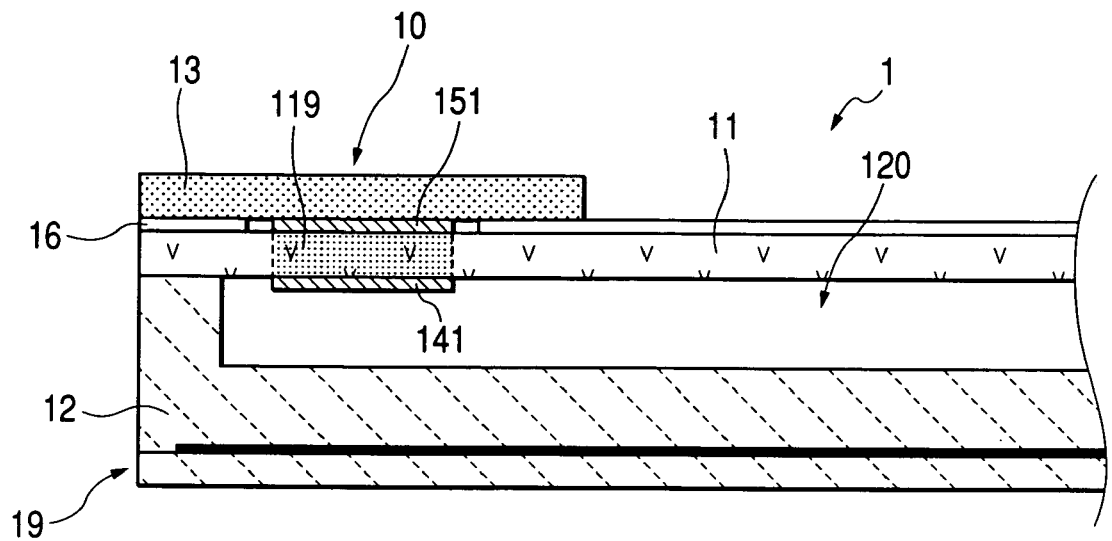
FIG. 2 is a longitudinal sectional view which shows the gas sensor element of FIG. 1.
Figure 3:
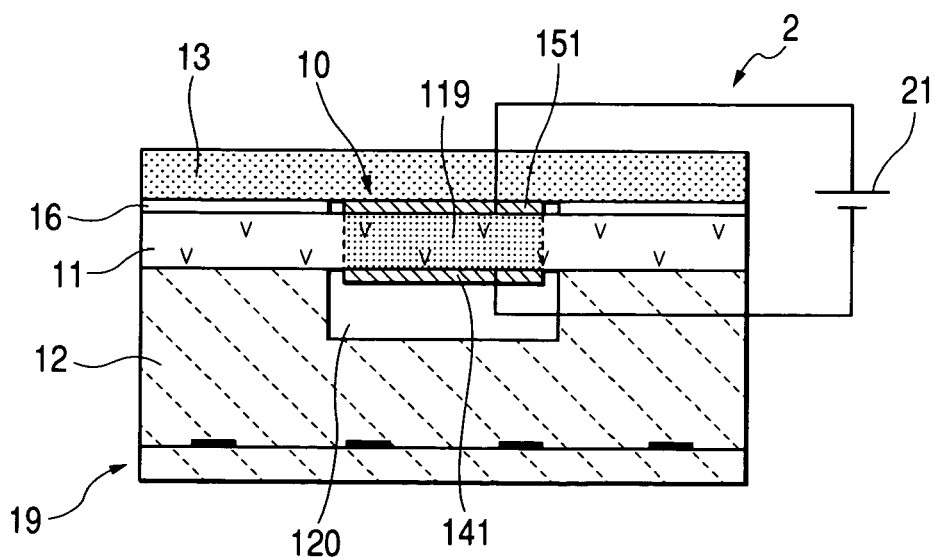
FIG. 3 is a transverse sectional view which shows the gas sensor element of FIG. 1.

Referring now to the drawings, wherein like numbers refer to like parts in several views, particularly to FIGS. 1, 2 and 3, there is shown a gas sensor element 1 according to the first embodiment of the invention which may be incorporated within a gas sensor installed in an exhaust pipe of an automotive engine to measure the concentration of oxygen ($O_2$) or an unburned component contained in exhaust gasses of the engine in order to determine an air-fuel ratio of a mixture supplied to combustion chambers of the engine for use in air-fuel ratio control. An overall structure of such a gas sensor is not essential, and explanation thereof in detail will be omitted here. For example, U.S. Pat. No. 5,573,650, issued Nov. 12, 1996 to Fukaya et al., teaches an oxygen sensor equipped with a laminated sensor element, disclosure of which is incorporated herein by reference.

The gas sensor element 1 is of a single cell structure which is equipped with an electrochemical cell 10 consisting of a solid electrolyte plate 11 made of a partially stabilized zirconia and a pair of electrodes 141 and 151. In production of the gas sensor element 1, an aging treatment is performed, as will be described later in detail, by applying the dc current to the electrochemical cell 10 through the electrodes 141 and 151.

Figure 6:
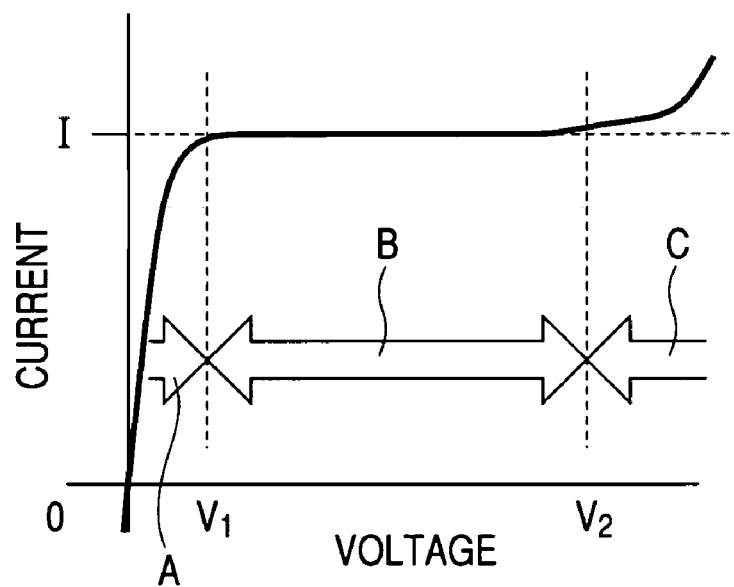
FIG. 6 is a graph which shows a voltage-current characteristic and a limiting current range of a gas sensor element.
Figure 7:
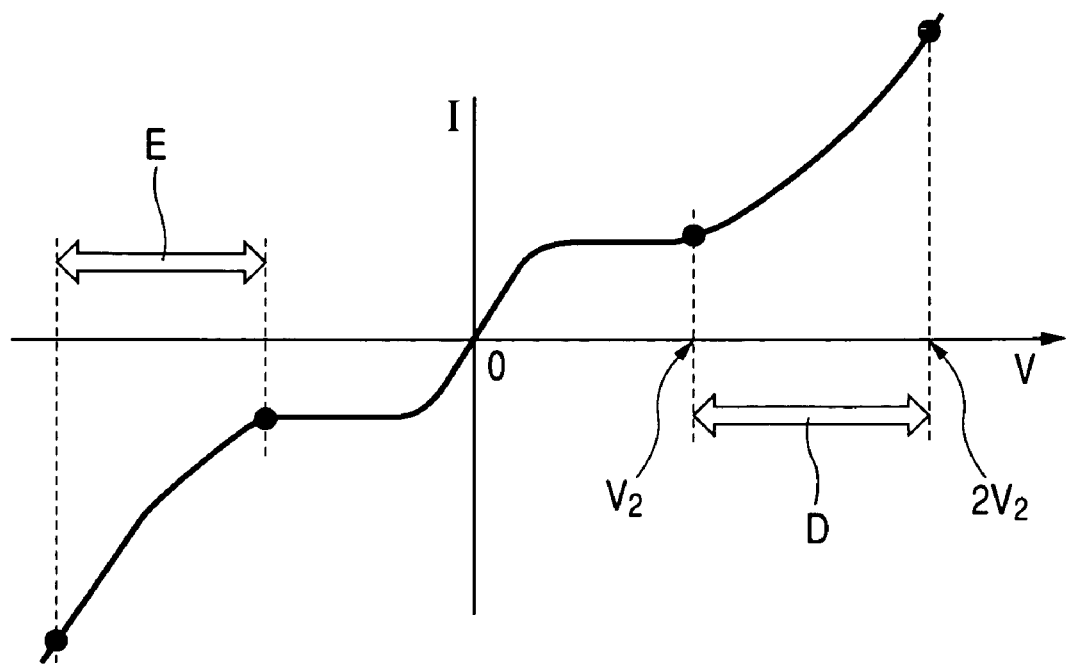
FIG. 7 is a graph which shows a limiting current of a gas sensor element and the magnitude of current flowing through the gas sensor element in an aging treatment.

The voltage V of the dc current used in the aging treatment is, as shown in FIG. 6, given by a relation of $V_2 \leq V \leq 2V_2$ where $V_2$ is a maximum voltage within a range where a limiting current is produced in the electrochemical cell 10. The voltage higher than $2V_2$ may cause a crystalline structure of zirconia of the electrochemical cell 10 to change greatly, thus resulting in a decrease in mechanical strength thereof, which, in the worst case, leads to breakage of the electrochemical cell 10.

Referring back to FIGS. 1 to 3, the gas sensor element 1 is a limiting current sensor element made of a laminate of a diffusion resistance layer 13, the solid electrolyte plate 11, a spacer 12, and a ceramic heater 19.

The gas sensor element 1 is, as described above, installed in, for example, an exhaust pipe of an automotive engine for use in the air-fuel ratio control. Specifically, the gas sensor element 1 works as the so-called A/F sensor to measure the concentration of oxygen within exhaust gasses in order to determine an air-fuel ratio of a mixture in a combustion chamber of the engine and has a single cell structure having the electrochemical cell 10.

The electrochemical cell 10 has the electrodes 141 and 151 jointed electrically to terminals 143 and 153 through leads 142 and 152, respectively. The electrode 141 is disposed between the spacer 12 and the solid electrolyte plate 11 and works as a reference gas electrode. The electrode 151 is covered with the diffusion resistance layer 13 and works as a measurement gas electrode. An insulating layer 16 is disposed on the solid electrolyte plate 11 and has formed therein an elongated opening or window 160 through which the electrode 151 faces the solid electrolyte plate 11. The insulating layer 16 is made of an insulating material such as alumina in order to avoid leakage of current from the leads 142 and 152. The window 160 defines a measurement gas chamber between the diffusion resistance layer 13 and the solid electrolyte plate 11 into which a gas to be measured by the gas sensor element 1 is admitted from outside the gas sensor element 1 through the diffusion resistance layer 13.

The electrode 141 communicates electrically with a terminal 145 disposed on the insulating layer 16 through the lead 142, the terminal 143, a through hole 144 formed in the solid electrolyte plate 11 and a through hole 161 formed in the insulating layer 16. The electrode 151 communicates electrically with the terminal 153 through the lead 152. Input to and output from the gas sensor element 1 is accomplished through the terminals 145 and 153.

Both or either of the electrodes 141 and 151 may be made of a cermet. For example, the electrodes 141 and 151 are made by coating the solid electrolyte plate 11 with paste of an organic substance or paste including an organic substance and some additive and burning it. The additive may be identical in material with the solid electrolyte plate 11.

The spacer 12 has formed therein a groove defining an air chamber 120 into which the air is admitted as a reference gas.

The ceramic heater 19 is made up of a base plate 191 and a heating element 190 disposed on the base plate 191. The heating element 190 is joined to leads 195 which lead electrically to terminals 197 through holes 196 formed in the base plate 191. The power is supplied to the heating element 190 through the terminals 197 to heat the gas sensor element 1 (i.e., the electrochemical cell 10) up to a desired activation temperature.

The solid electrolyte plate 11, as clearly shown in FIGS. 2 and 3, has a discolored portion 119 between the electrodes 141 and 151. The solid electrolyte plate 11 is gray or light brown in color as a whole, while the discolored portion 119 is dark brown which is visually distinguishable. The discolored portion 119 may occupy 80% of a portion of the solid electrolyte plate 11 which is sandwiched between the electrodes 141 and 151 and through which oxygen ions pass.

Production steps of the gas sensor element 1 will be described below in detail.

First, a partially stabilized zirconia green sheet for forming the solid electrolyte plate 11 is prepared:

Yttria/partially stabilized zirconia powders are prepared. A suitable weight of a PVB (polyvinylbutyral) working as binder is added to the yttria/partially stabilized zirconia powders and mixed together in a ball mill to make slurry.

The slurry is formed using a doctor blade into a sheet of a predetermined thickness. The sheet is cut to a desired size to make a green sheet. A pin hole (i.e., the through hole 144) is formed in the green sheet. The pin hole is filled with a conductive paste such as Pt. A given area of the green sheet is coated with an alumina paste using screen printing techniques to make the insulating layer 16. Next, a Pt paste is applied using the screen printing techniques to make the electrodes 141 and 151 and the leads 142 and 152. This makes the electrochemical cell 10.

Subsequently, alumina green sheets for making the heater base 191 and the spacer 12 are prepared in the following manner.

A suitable weight of PVB working as binder is added to alumina powder and mixed together in a ball mill to make slurry.

Next, the slurry is formed using the doctor blade into two sheets: one having a given thickness of the heater base 191 and the other having a given thickness of the spacer 12. The sheets are cut to desired sizes to make a heater green sheet and a spacer green sheet. Pin holes are formed in the heater green sheet to make the through holes 196 and filled with a conductive paste such as Pt.

The heating element 190, the leads 195, the terminals 197 are printed using a Pt paste to complete the ceramic heater 19.

The air chamber 120 is formed in the spacer green sheet by cutting and pressing to complete the spacer 12.

The slurry is made using alumina powder which is inferior to the base plate 191 of the heater 19 and the spacer 12 in the degree of sintering. The slurry is formed to a desired thickness using the doctor blade and cut to a desired size to a green sheet for making the diffusion resistance layer 13.

The green sheets and unburned laminate produced in the above manner are laid to overlap each other in the order, as illustrated in FIG. 1, pressed, and bonded together. This laminate is then baked at 1400° C. to 1500° C. to make the gas sensor element 1.

Finally, an aging treatment circuit 2 equipped with a power supply 21, as illustrated in FIG. 3, is joined to the electrodes 141 and 151 of the gas sensor element 1. The dc current is supplied to the gas sensor element 1 at 2V for 60 minutes to form the discolored portion 119.

We prepared the gas sensor element 1 produced in the above manner and a gas sensor element sample which does not have the discolored portion 119 and performed tests, as discussed below, to determine a voltage-current relation in terms of the temperature thereof.

+2V was applied to electrodes of the gas sensor element sample for 30 minutes, after which −2V was applied thereto for 30 minutes.

Next, each of the gas sensor element 1 and the gas sensor element sample was built into the gas sensor and exposed to the air. The ceramic heater 19 was excited to increase the temperature of each of the gas sensor element 1 and the gas sensor element sample up to 700° C., 800° C., and 900° C.

Figure 4:
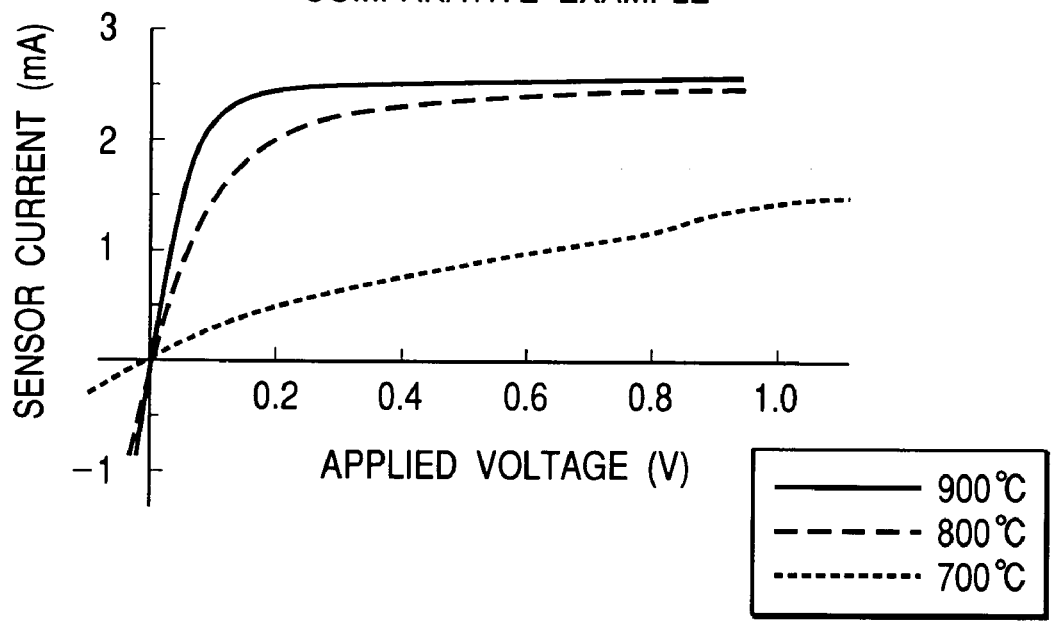
FIG. 4 is a graph which represents a relation between voltage applied to an comparative example of a gas sensor element and a resulting current flowing therethrough.
Figure 5:
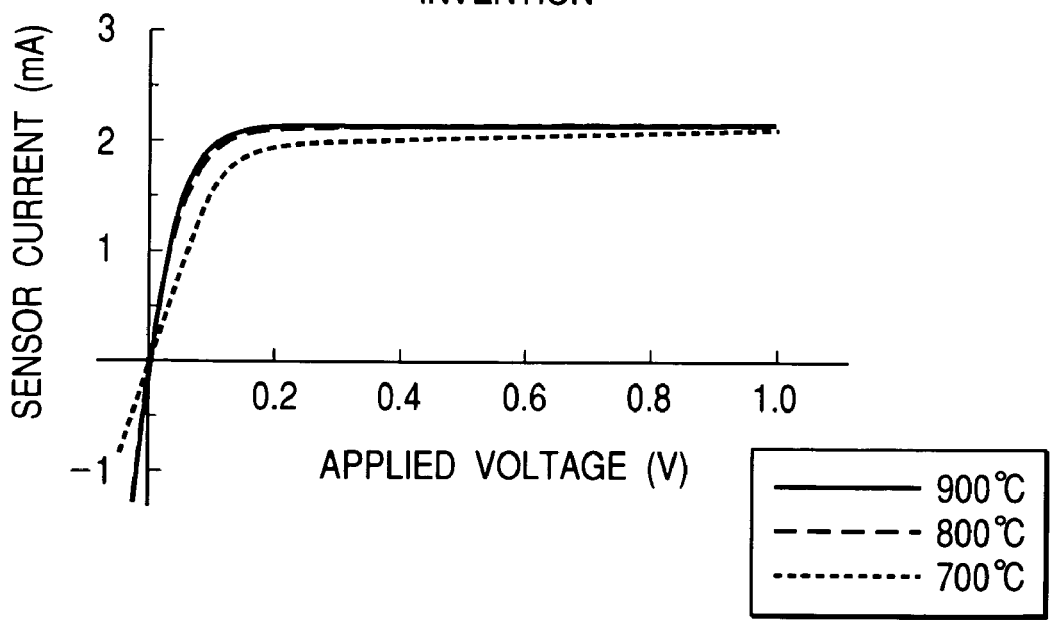
FIG. 5 is a graph which represents a relation between voltage applied to the gas sensor element of FIG. 1 and a resulting current flowing therethrough.

At each of 700° C., 800° C., and 900° C., the electrochemical cell 10 of each of the gas sensor element 1 and the gas sensor element sample was exited to measure the voltage applied thereto and current flowing therethrough, as illustrated in FIGS. 4 and 5.

The graphs of FIGS. 4 and 5 show that in the case of 900° C., the limiting current is substantially kept constant (i.e., within a maximum amplitude change of 10% within a voltage change of 0.1V) when the applied voltage is higher than 0.1V regardless of the discolored portion 119, and in the cases of 700° C. and 800° C., the gas sensor element 1 has substantially the same limiting current range as that in the case of 900° C., but the gas sensor element sample changes greatly in voltage-current characteristic, thus resulting in decreased accuracy of measuring the concentration of oxygen at 700° C. and 800° C.

The gas sensor element 1 of this embodiment is, as described above, subjected to the aging treatment in a production process to discolor a portion of the solid electrolyte plate 11, as indicated at 119 in FIGS. 2 and 3, between the electrodes 141 and 151 of the electrochemical cell 10. The discolored portion 119 is higher in degree of activation, thereby enabling the concentration of oxygen to be measured accurately at lower temperatures.

Use of the gas sensor element 1 in a gas sensor installed in an exhaust pipe of an automotive engine, thus, enables the concentration of oxygen ($O_2$) contained in exhaust gasses to be measured within a decreased period of time (about 5 minutes) following start up of the engine. This makes it possible to perform air-fuel ratio control accurately immediately after the startup of the engine, thereby facilitating removable of air pollutants from the exhaust gasses through a three-way catalytic converter.

The above described aging treatment may also be performed on a gas sensor element equipped with a cup-shaped solid electrolyte body, as will be described later in FIG. 4, or a two-cell gas sensor element, as will be described later in FIG. 6.

The present invention is not limited to the A/F sensor and may alternatively be used with a variety of gas sensors such as NOx, HC, and CO sensors (see the fifth embodiment as discussed later).

While the aging treatment is, as described above, performed using the voltage V between $V_2$ and $2V_2$, the voltage V lies preferably within a range of $1.2V_2$ to $1.5V_2$.

The aging treatment is preferably performed while the temperature of the gas sensor element 1 is kept at 500° C. to 1000° C. using, for example, the heater 19.

When the temperature is less than 500° C., it results in a great variation in $V_2$ between individual gas sensor elements, thereby making it difficult to apply the dc current to the electrochemical cell 10 of all the gas sensor elements at the voltage V of $V_2$ to $2V_2$.

When the temperature is more than 1000° C., it results in a great variation in degree of the current flowing through the electrochemical cell 10 upon application of the voltage V, which leads to a great variation in performance between individual gas sensor elements.

The application of the dc voltage to the electrochemical cell 10 is kept preferably for approximately 30 seconds to 15 minutes. In a case of less than 30 seconds, the solid electrolyte plate 11 and the electrodes 141 and 151 may not be activated sufficiently. In a case of more than 15 minutes, the mechanical strength of the gas senor element 1 may be decreased. The power consumed in the aging treatment is also increased, thus resulting in an increase in manufacturing cost of the gas sensor element 1.

If a value of the limiting current at 700° C. in the air is defined as $I_{700}$, and a value of the limiting current at 900° C. in the air is defined as $I_{900}$, it is advisable that a condition of $0.8 \times I_{900} \leq I_{700} \leq 1.2 \times I_{900}$ be met. This results in a small change in output of the gas sensor element 1 regardless of a change in temperature of the gas sensor element 1, thereby increasing the measurement accuracy of the gas sensor element 1.

The second embodiment will be described below which is different from the first embodiment in condition of the aging treatment.

We prepared some gas sensor element samples identical in structure with the gas sensor element 1 of the first embodiment and perform the aging treatment on them. The aging treatment was achieved by applying the dc current to the gas sensor element samples at $0.9V_2$ to $4V_2$, respectively, for one (1) minute. We also prepared a comparative sample not subjected to the aging treatment.

We determined a relation between the temperature of each sample and the current flowing between the reference gas electrode 141 and the measurement gas electrode 151 of each sample in the following manner. 0.4V was applied across the reference gas electrode (+) and the measurement gas electrode (−) in the air to decrease the activation temperature. Next, the heater 19 was excited to increase the temperature of each sample up to a desired value by adjusting the power supplied to the heater 19 while monitoring the reading on a radiation thermometer.

The current flowing through the electrodes 141 and 151 of the electrochemical cell 10 increased with an increase in temperature of each sample. Note that the temperature of each sample when the current flowing between the electrodes 141 and 151 of the cell 10 reaches $0.8 \times IL_{800}$ is defined as the activation temperature where $IL_{800}$ is the current when the temperature of each sample is 800° C. A relation between the activation temperature and voltage applied to each sample is illustrated in FIG. 8.

Figure 8:
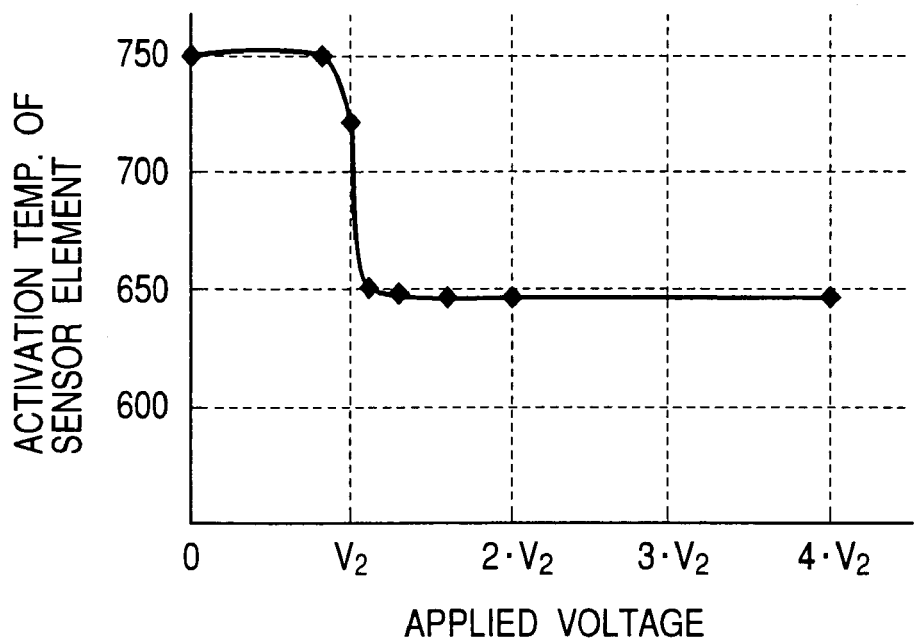
FIG. 8 is a graph which shows a relation between voltage used in an aging treatment and an activation temperature of a gas sensor element in the second embodiment of the invention.

FIG. 8 shows that the aging treatment using an applied voltage of $V_2$ or more results in a great decrease in the activation temperature.

Figure 9:
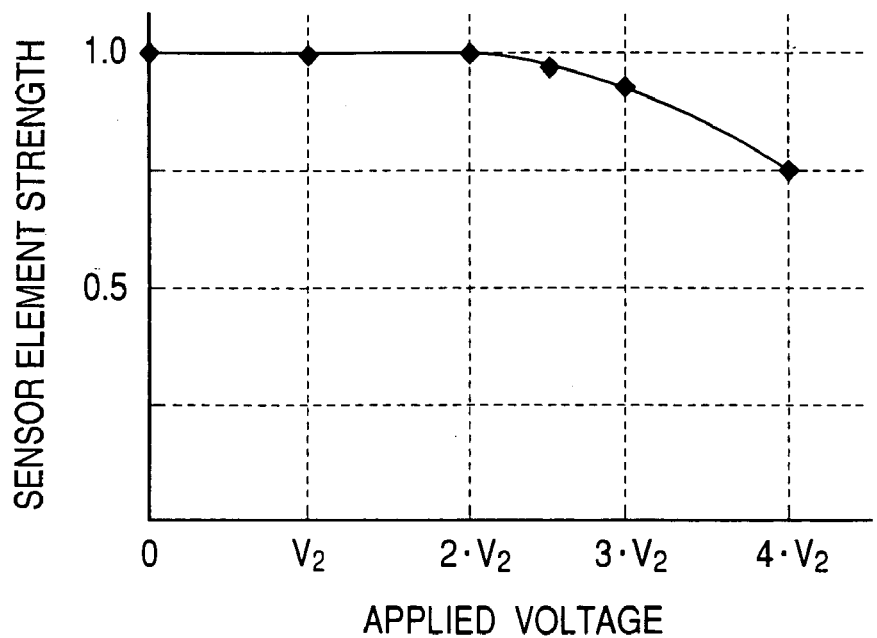
FIG. 9 is a graph which shows a relation between voltage used in an aging treatment and mechanical strength of a gas sensor element in the second embodiment of the invention.

We also prepared the same samples as described above and performed the aging treatment for ten (10) minutes by supplying a dc current to each sample at $V_2$ or more. After the aging treatment, the diffusion resistance layer 13 was removed by grinding to expose the surface of the partially stabilized zirconia body. The diffusion resistance layer 13 was not removed from the comparative sample not subjected to the aging treatment. We pressed the center of the measurement gas electrode 151 using a pin and measured the load at which the partially stabilized zirconia was broken. Test results are shown in FIG. 9. The sensor element strength is expressed by a ratio of the strength of each gas sensor element sample to that of the comparative sample which is defined as 1.0.

The graph of FIG. 9 shows that an increase in the voltage used in the aging treatment results in a decrease in mechanical strength of each sample. It is, thus, advisable that the voltage used in the aging treatment be adjusted in terms of purposes of use of the gas sensor element 1.

Figure 10:
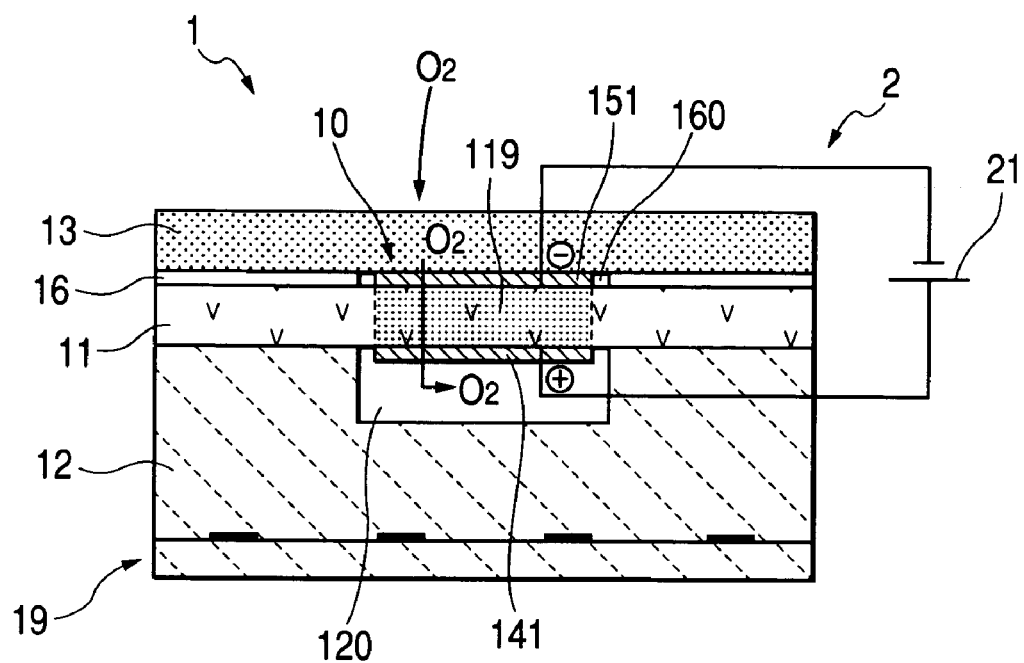
FIG. 10 is a transverse sectional view which shows a gas sensor element subjected to an aging treatment according to the third embodiment of the invention.

The third embodiment will be described below using FIG. 10 which is different from the first embodiment in condition of the aging treatment.

The aging treatment of this embodiment is performed in the following manner. The reference gas electrode 141 exposed to air in the air chamber 120 is connected to a positive terminal of the power supply of the aging treatment circuit 2, while the measurement gas electrode 151 exposed to a measurement gas introduced into the window 160 through the diffusion resistance layer 13 is connected to a negative terminal of the power supply of the aging treatment circuit 2. The dc current is supplied to the electrodes 141 and 151. This causes oxygen molecules within the window 160 to be ionized and go to the electrode 141 from the electrode 151. Specifically, an oxygen ion current flows from the electrode 151 to the electrode 141, so that oxygen joined to the electrode 151 is removed therefrom, thus resulting in an increased degree of activation of the electrode 151. This increases the efficiency of ionizing oxygen molecules on the electrode 151 of the gas sensor element 1 when the concentration of oxygen is measured, which leads to a decrease in the activation temperature.

We prepared a first gas sensor element sample subjected to the aging treatment in the same manner as described in the first embodiment, a second gas sensor element sample subjected to the aging treatment of this embodiment, and a comparative sample not subjected to the aging treatment and measured the activation temperatures thereof in the manner as described in the second embodiment. The aging treatment of each of the first and second gas sensor element samples was achieved using $1.5V_2$. We found that the activation temperatures of the first gas sensor element sample, the second gas sensor element sample, and the comparative sample is 650° C., 630° C., and 750° C., respectively, and that the aging treatment of this embodiment serves to speed up the activation of the gas sensor element 1.

Figure 11:
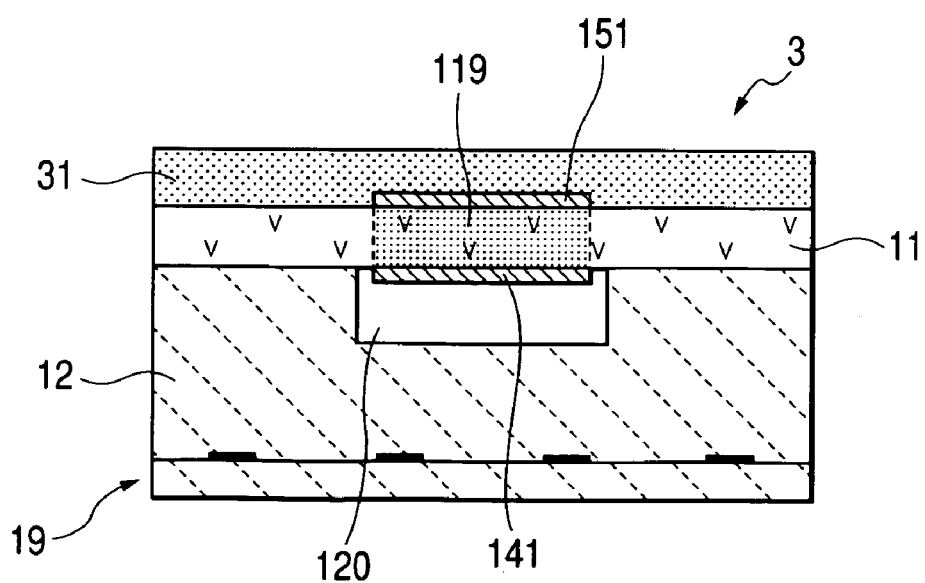
FIG. 11 is a transverse sectional view which shows an electromotive force gas sensor element according to the fourth embodiment of the invention.

The fourth embodiment will be described below in which the aging treatment is performed on an electromotive force gas sensor element 3 as illustrated in FIG. 11.

The gas sensor element 3 is made of a laminate of the porous protective layer 31, the solid electrolyte plate 11, the spacer 12, and the ceramic heater 19.

The solid electrolyte plate 11 has the electrodes 141 and 151. The electrode 141 is, like the first embodiment, exposed to the air chamber 120 and works as a reference gas electrode. The electrode 151 is covered with the porous protective layer 31 and exposed to a gas to be measured.

The gas sensor element 3 is designed to produce a potential difference between the electrodes 141 and 151 as a function of a difference in oxygen concentration of the reference gas and the measurement gas. The concentration of oxygen ($O_2$) to which the electrode 151 is exposed is determined as a function of the potential difference.

The porous protective layer 31 has a porosity of 18% and is more porous than the diffusion resistance layer 13 of the gas sensor element 1 of the first embodiment. The porosity of the diffusion resistance layer 13 is, for example, 14%.

Figure 12:
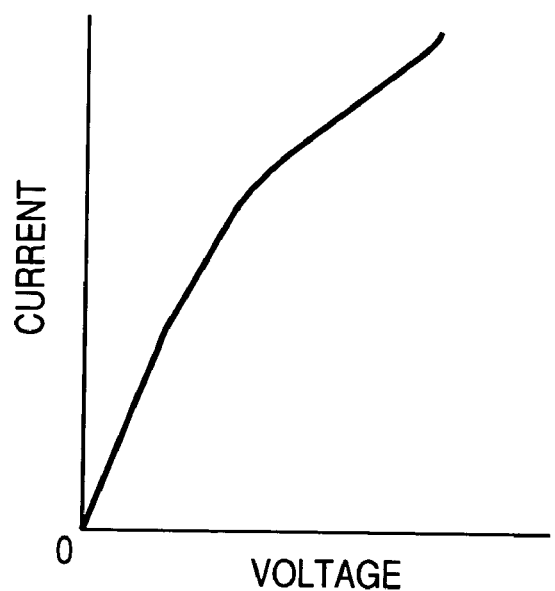
FIG. 12 is a graph which shows a voltage-current relation of the gas sensor element of FIG. 11 within the air.
Figure 13:
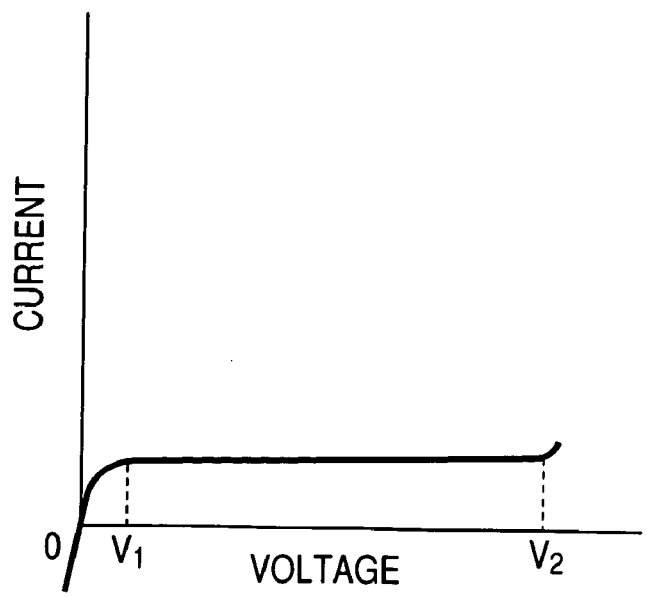
FIG. 13 is a graph which shows a voltage-current relation of the gas sensor element of FIG. 11 within an atmosphere where the oxygen concentration is less than 0.1%.

The voltage-current characteristic of the gas sensor element 3 in the air is shown in FIG. 12. The current flows substantially as a function of the voltage according to the Ohm's law. The porous protective layer 31 somewhat exhibits the effects of orifices. Therefore, when the concentration of oxygen is considerably low (e.g., 0.1%), as shown in FIG. 13, a clear limiting current range appears at the voltage-current characteristic. Using the voltage $V_2$ determined using the voltage-current characteristic obtained in the atmosphere where the concentration of oxygen is low, the same aging treatment as described in the first or third embodiments is performed on the gas sensor element 3 within the atmosphere where the concentration of oxygen is very low. This provides substantially the same effect of the aging treatment as that in the above embodiments.

The aging treatment may also be performed in an oxygen free atmosphere including 100% of nitrogen or under vacuum.

Other arrangements of the gas sensor element 3 are identical with those in the first embodiment, and explanation thereof in detail will be omitted here.

Figure 14:
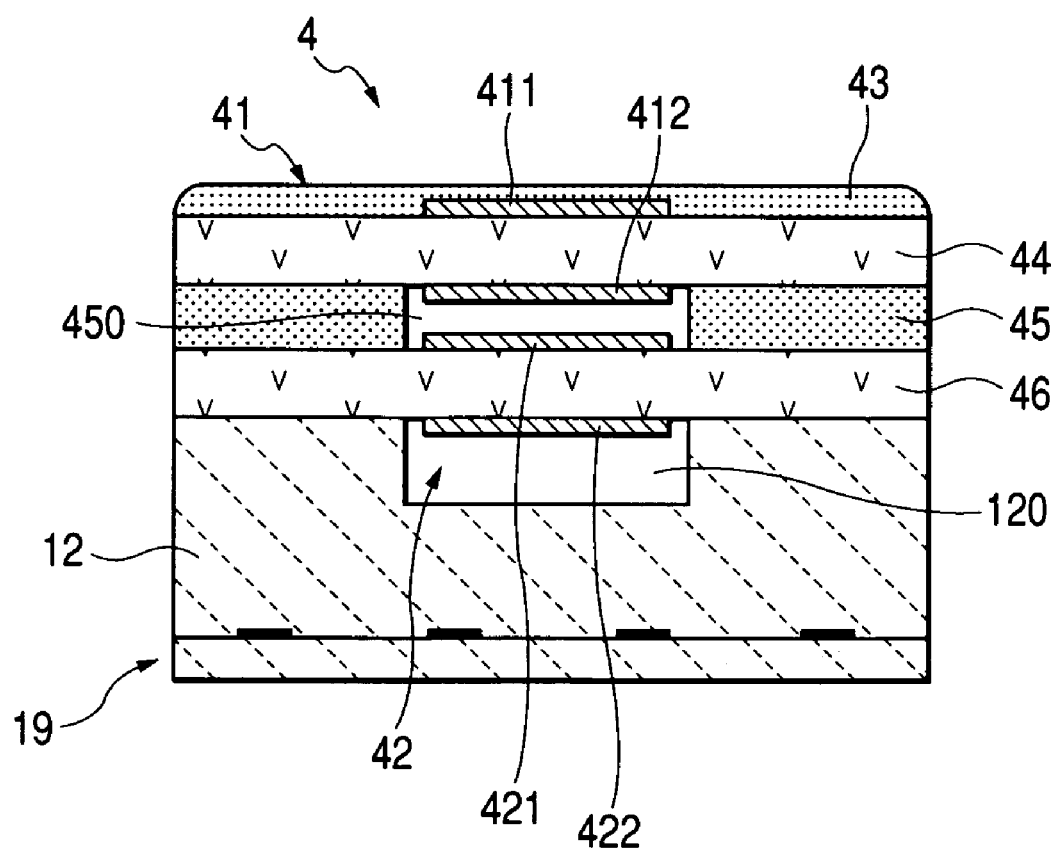
FIG. 14 is a transverse sectional view which shows a two-cell gas sensor element according to the fifth embodiment of the invention.

The fifth embodiment will be described below in which the aging treatment is performed on a two-cell gas sensor element 4, as illustrated in FIG. 14.

The gas sensor element 4 has a two-cell structure made of a laminate of a porous protective layer 43, solid electrolyte plates 44 and 46, spacers 45 and 12, and the ceramic heater 19 and works to measure the concentration of NOx contained in, for example, exhaust gasses of the engine.

The gas sensor element 4 has a first electrochemical cell 41 and a second electrochemical cell 42. The first electrochemical cell 41 consists of the solid electrolyte plate 44 and a pair of electrodes 411 and 412. The electrode 411 is exposed to the measurement gas (i.e., NOx) through the porous protective layer 43. The electrode 412 is exposed to a measurement gas chamber 450 formed in the spacer 45. The spacer 45 is made of a porous alumina ceramic which permits the measurement gas to be admitted into the measurement gas chamber 450.

The second electrochemical cell 42 consists of the solid electrolyte plate 46 and a pair of electrodes 421 and 422. The electrode 421 is exposed to the measurement gas chamber 450. The electrode 422 is exposed to the air chamber 120 into which the air is admitted.

In operation, application of voltage to the first electrochemical cell 41, it will cause the first electrochemical cell 41 to pump oxygen ($O_2$) from the measurement gas chamber 450 to outside the sensor element 4 and vice versa to decrease the concentration of oxygen within the measurement gas chamber 450 to substantially zero (0) or keep it at a given constant level.

The electrode 421 of the second electrochemical cell 42 is capable of being activated to ionize or dissolve NOx into a nitrogen ion and an oxygen ion. Application of voltage to the second electrochemical cell 42 through the electrodes 421 and 422 will cause an oxygen ion arising from the dissolution of NOx to travel from the electrode 421 to the electrode 422 through the solid electrolyte plate 46. A determination of the concentration of NOx within the measurement gas chamber 450 is, thus, accomplished by adjusting the concentration of oxygen within the measurement gas chamber 450 to a preselected value through the first electrochemical cell 41 and measuring the current flowing through the second electrochemical cell 42 by the application of voltage thereto.

The aging treatment is, like the above embodiments, performed on the gas sensor element 4 by applying a dc current to the electrodes 411 and 412 of the first electrochemical cell 41 and the electrodes 421 and 422 of the second electrochemical cell 42, thereby improving the activation of the first and second electrochemical cells 41 and 42 to decrease the activation temperature of the first and second electrochemical cells 41 and 42. The application of the dc current to the first and second electrochemical cells 41 and 42 may be achieved by joining the electrodes 411 and 422 to a positive terminal of a power supply of an aging treatment circuit (not shown), thereby decreasing the activation temperature of the first and second electrochemical cells 41 and 42 greatly.

The aging treatment may be performed only on either of the first and second electrochemical cells 41 and 42 to facilitate the activation thereof.

A gas sensor element according to the sixth embodiment of the invention will be described below. The gas sensor element has substantially the same structure as that of the fifth embodiment and will be discussed with reference to FIG. 14.

The gas sensor element 4 of this embodiment is incorporated within a gas sensor installed in an exhaust pipe of an automotive internal combustion engine and works to measure the concentration of oxygen ($O_2$) contained within exhaust gasses for determining an air-fuel ratio of a mixture in the engine.

The electrode 421 of the second electrochemical cell 42, unlike the fifth embodiment, needs not have the ability of ionizing or dissolving NOx.

The first electrochemical cell 41 is responsive to application of voltage thereto to pump oxygen ($O_2$) from the measurement gas chamber 450 to outside the sensor element 4 and vice versa, thereby causing an oxygen ion current Ip to flow through the electrodes 411 and 412. The second electrochemical cell 42 works to produce an electromotive force Vs between the electrodes 421 and 422 as a function of a difference in concentration of oxygen within the measurement gas chamber 450 and the air chamber 120. The oxygen iron current Ip changing as a function of the air-fuel ratio is produced by adjusting the voltage applied to the electrodes 411 and 412 of the first electrochemical cell 41 to keep the concentration of oxygen within the measurement gas chamber 450 at a constant value so that the electromotive force Vs may be kept constant. A determination of the air-fuel ratio is, thus, made by measuring the thus produced oxygen iron current Ip.

Figure 15:
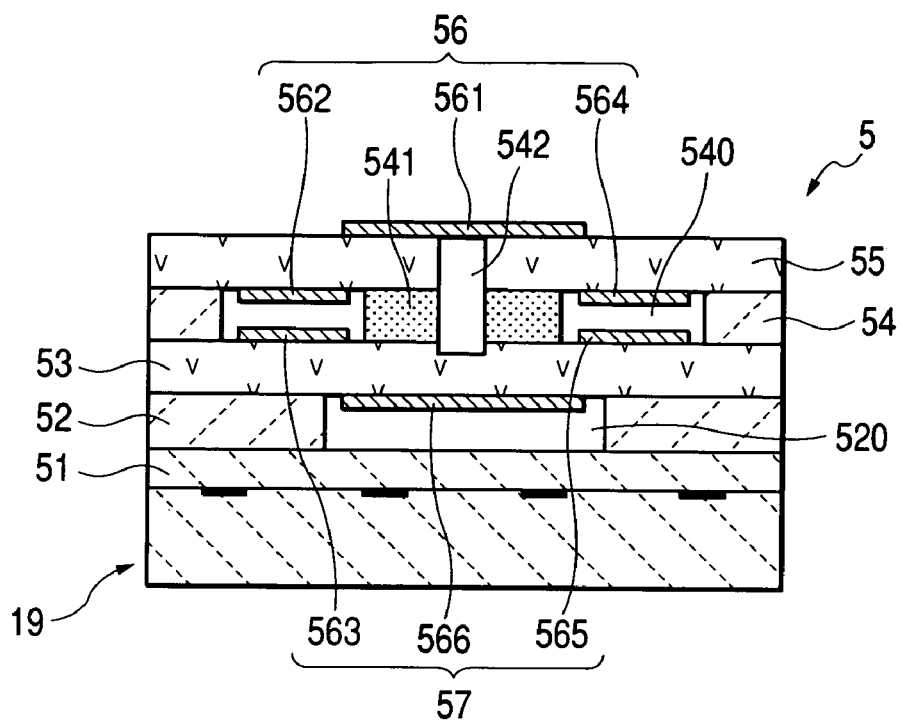
FIG. 15 is a transverse sectional view which shows a two-cell gas sensor element according to the seventh embodiment of the invention.

FIG. 15 shows a gas sensor element 5 according to the seventh embodiment of the invention which has a two-cell structure with pairs of electrodes.

The gas sensor element 5 is made of a laminate of solid electrolyte plates 53 and 55, spacers 52 and 54, an insulating plate 51, and the ceramic heater 19 and works to measure the concentration of NOx contained in, for example, exhaust gasses of an automotive internal combustion engine.

The gas sensor element 4 has a first electrochemical cell 56 and a second electrochemical cell 57. The first electrochemical cell 56 consists of the solid electrolyte plate 55 and a set of electrodes 561, 562, and 563. The electrode 561 is exposed directly to the measurement gas (i.e., NOx). The electrodes 562 and 563 are exposed to a measurement gas chamber 540. The measurement gas chamber 540 is formed in the spacer 54 into which the measurement gas flows through a hole 542 formed in through the solid electrolyte plate 55 and the porous layer 541.

The second electrochemical cell 57 consists of the solid electrolyte plate 53 and a set of electrodes 563, 565, and 566. The electrodes 563 and 565 are exposed to the measurement gas chamber 540. The electrode 566 is exposed to the air chamber 520 into which the air is admitted. The air chamber 520 is defined by the spacer 52 and the insulating plate 51.

In operation, application of voltage to the first electrochemical cell 56, it will cause the first electrochemical cell 56 to pump oxygen ($O_2$) from the measurement gas chamber 540 to outside the sensor element 5 and vice versa to decrease the concentration of oxygen within the measurement gas chamber 540 to substantially zero (0) or keep it at a given constant level.

The electrodes 563 and 565 of the second electrochemical cell 57 are capable of being activated to ionize or dissolve NOx into a nitrogen ion and an oxygen ion. Application of voltage to the second electrochemical cell 57 through the electrodes 563, 566, and 565, it will cause oxygen ions arising from the dissolution of NOx to travel from the electrodes 563 and 565 to the electrode 566 through the solid electrolyte plate 53. A determination of the concentration of NOx within the measurement gas chamber 540 is, thus, accomplished by adjusting the concentration of oxygen within the measurement gas chamber 540 to a preselected value through the first electrochemical cell 56 and measuring the current flowing through the second electrochemical cell 57 by the application of voltage thereto.

The aging treatment is, like the first and fifth embodiments, performed on the gas sensor element 5 by applying dc currents across the electrodes 561 and 562 and across the electrodes 561 and 564 of the first electrochemical cell 56 and across the electrodes 566 and 563 and across the electrodes 566 and 565 of the second electrochemical cell 57, thereby improving the activation of the first and second electrochemical cells 56 and 57 to decrease the activation temperature of the first and second electrochemical cells 56 and 57.

The aging treatment may be performed only on either of the first and second electrochemical cells 56 and 57 to facilitate the activation thereof.

Other arrangements are identical with those in the first or fifth embodiments, and explanation thereof in detail will be omitted here.

A gas sensor element according to the eighth embodiment of the invention will be described below. The gas sensor element has a two-cell structure identical with that of the seventh embodiment and will be discussed with reference to FIG. 15.

The gas sensor element 5 of this embodiment is incorporated within a gas sensor installed in an exhaust pipe of an automotive internal combustion engine and works to measure the concentration of oxygen ($O_2$) contained within exhaust gasses for determining an air-fuel ratio of a mixture in the engine.

The electrodes 563 and 564, unlike the seventh embodiment, need not have the ability of ionizing or dissolving NOx.

The first electrochemical cell 56 is responsive to application of voltage thereto to pump oxygen ($O_2$) from the measurement gas chamber 540 to outside the sensor element 5 and vice versa, thereby causing an oxygen ion current Ip to flow through the first electrochemical cell 56. The second electrochemical cell 57 works to produce an electromotive force Vs between the electrodes 566 and 563 and between the electrodes 566 and 565 as a function of a difference in concentration of oxygen within the measurement gas chamber 540 and the air chamber 520. The oxygen iron current Ip changing as a function of the air-fuel ratio is produced by adjusting the voltage applied to the electrodes 561, 562 and 564 of the first electrochemical cell 56 to keep the concentration of oxygen within the measurement gas chamber 540 at a constant value so that the electromotive force Vs may be kept constant. A determination of the air-fuel ratio is, thus, made by measuring the thus produced oxygen iron current Ip.

The aging treatment is, like the first and fifth embodiments, performed on the gas sensor element 5 by applying dc currents across the electrodes 561 and 562 and across the electrodes 561 and 564 of the first electrochemical cell 56 and across the electrodes 566 and 563 and across the electrodes 566 and 565 of the second electrochemical cell 57, thereby improving the activation of the first and second electrochemical cells 56 and 57 to decrease the activation temperature of the first and second electrochemical cells 56 and 57.

The aging treatment may be performed only on either of the first and second electrochemical cells 56 and 57 to facilitate the activation thereof.

Other arrangements are identical with those of the first or fifth embodiment, and explanation thereof in detail will be omitted here.

Figure 16:
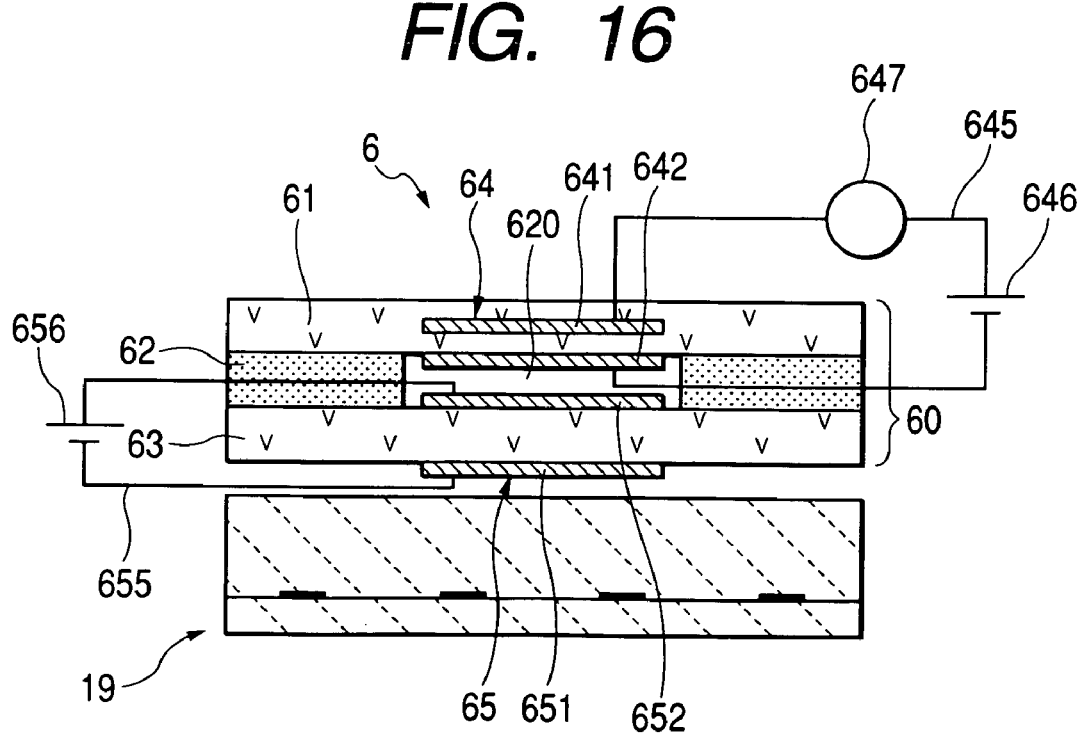
FIG. 16 is a transverse sectional view which shows a two-cell gas sensor element with a separate ceramic heater according to the ninth embodiment of the invention.

FIG. 16 shows a gas sensor element 6 according to the ninth embodiment of the invention which has a separate ceramic heater 19 and no reference gas chamber.

The gas sensor element 6 is made up of the ceramic heater 19 and a sensor element body 60. The sensor element body 60 consists of solid electrolyte plates 61 and 63 and a spacer 62 and works to measure the concentration of NOx contained in, for example, exhaust gasses of an automotive internal combustion engine.

The gas sensor element 6 has a first electrochemical cell 64 and a second electrochemical cell 65. The first electrochemical cell 64 consists of the solid electrolyte plate 61 and a pair of electrodes 641 and 642. The electrode 641 is embedded within the solid electrolyte plate 61. The electrode 642 is exposed to a measurement gas chamber 620 formed in the spacer 62. The spacer 62 is made of a porous alumina ceramic which permits the measurement gas (i.e., NOx) to be admitted into the measurement gas chamber 620.

The second electrochemical cell 65 consists of the solid electrolyte plate 63 and a pair of electrodes 651 and 652. The electrode 652 is exposed to the measurement gas chamber 620. The electrode 651 is exposed directly to an atmosphere including the measurement gas existing between the ceramic heater 19 and the sensor element body 60.

In operation, application of voltage to the electrodes 651 and 562 of the second electrochemical cell 65 using a control circuit 655 equipped with a power supply 656, it will cause the second electrochemical cell 65 to pump oxygen ($O_2$) from the measurement gas chamber 620 to outside the sensor element 6 and vice versa to decrease the concentration of oxygen within the measurement gas chamber 620 to substantially zero (0) or keep it at a given constant level.

The electrode 642 of the first electrochemical cell 64 is capable of being activated to ionize or dissolve NOx into a nitrogen ion and an oxygen ion. The first electrochemical cell 64 is joined electrically through the electrodes 641 and 642 to a control circuit 645 equipped with a power supply 646 and a detector 647. Application of voltage to the first electrochemical cell 64 through the control circuit 645, it will cause oxygen ions arising from the dissolution of NOx to travel from the electrode 642 to the electrode 641 through the solid electrolyte plate 61. A determination of the concentration of NOx within the measurement gas chamber 620 is, thus, made by adjusting the concentration of oxygen within the measurement gas chamber 620 to a preselected value through the second electrochemical cell 65 and measuring the current flowing through the first electrochemical cell 64 using the detector 647 of the control circuit 645.

The aging treatment is, like the first and fifth embodiments, performed on the gas sensor element 6 by applying dc currents across the electrodes 641 and 642 of the first electrochemical cell 64 and across the electrodes 651 and 652 of the second electrochemical cell 65, thereby improving the activation of the first and second electrochemical cells 64 and 65 to decrease the activation temperature of the first and second electrochemical cells 64 and 65.

The aging treatment may be performed only on either of the first and second electrochemical cells 64 and 65 to facilitate the activation thereof.

Other arrangements are identical with those in the first, fifth, or seventh embodiment, and explanation thereof in detail will be omitted here.

A gas sensor element according to the tenth embodiment of the invention will be described below. The gas sensor element has a two-cell structure identical with that of the ninth embodiment and will be discussed with reference to FIG. 16.

The gas sensor element 6 of this embodiment is incorporated within a gas sensor installed in an exhaust pipe of an automotive internal combustion engine and works to measure the concentration of oxygen ($O_2$) contained within exhaust gasses for determining an air-fuel ratio of a mixture in the engine.

In operation, application of voltage to the second electrochemical cell 65 through the control circuit 655, it will cause the second electrochemical cell 65 to pump oxygen ($O_2$) from the measurement gas chamber 620 to outside the sensor element 6 and vice versa, thereby causing an oxygen ion current Ip to flow through the second electrochemical cell 65.

Application of weak voltage across the electrodes 642 and 641 of the first electrochemical cell 64 through the control circuit 645, it will cause oxygen molecules near the electrode 642 to be ionized, which, in turn, move to the electrode 641, thereby causing a potential difference Vs to be developed across the electrodes 641 and 642. The potential difference Vs is measured by the detector 647. The oxygen iron current Ip changing as a function of the air-fuel ratio is produced by adjusting the oxygen ion current Ip so as to keep the potential difference Vs constant so that the concentration of oxygen within the measurement gas chamber 620 is kept constant. A determination of the air-fuel ratio is, thus, made by measuring the thus produced oxygen iron current Ip.

Figure 17:
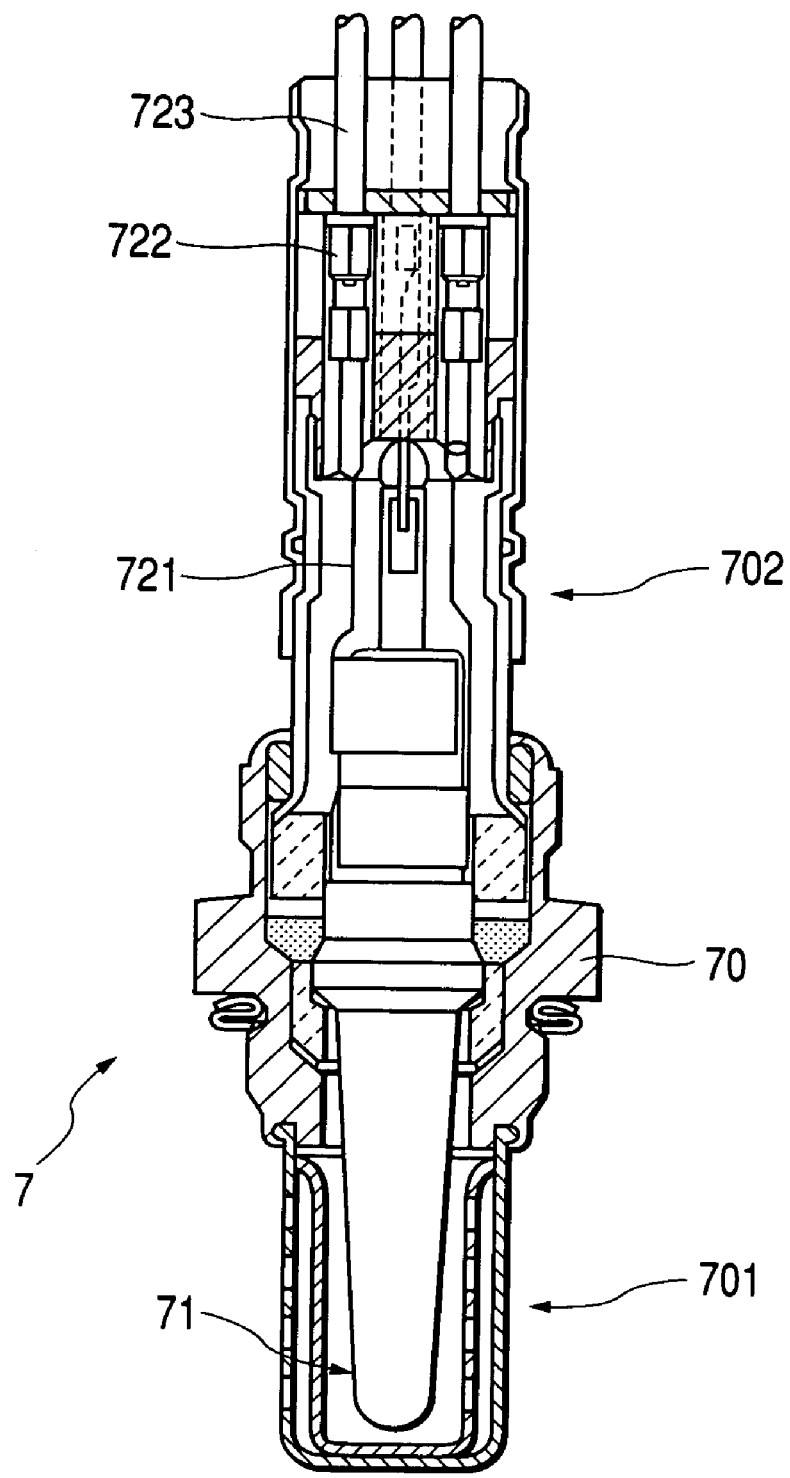
FIG. 17 is a longitudinal sectional view which shows a gas sensor in which a cup-shaped gas sensor element according to the eleventh embodiment of the invention is installed.

The eleventh embodiment will be described below in which the aging treatment is performed on a cup-shaped gas sensor element 71, as illustrated in FIG. 17.

The gas sensor element 71 is, as clearly shown in FIG. 17, installed within a housing 70 of a gas sensor 7.

The gas sensor element has a head portion protected by a measurement gas cover assembly 701 and a base portion protected by an air cover 702. Within the air cover 702, the gas sensor element 71 is connected electrically to an external control circuit (not shown) through lead terminals 721, connector terminals 722, and leads 723. The external control circuit is equipped with a power supply and an ammeter and works to measure the current arising from application of the voltage to the gas sensor element 71 to determine the concentration of oxygen ($O_2$) within the measurement gas cover assembly 701.

Figure 18:
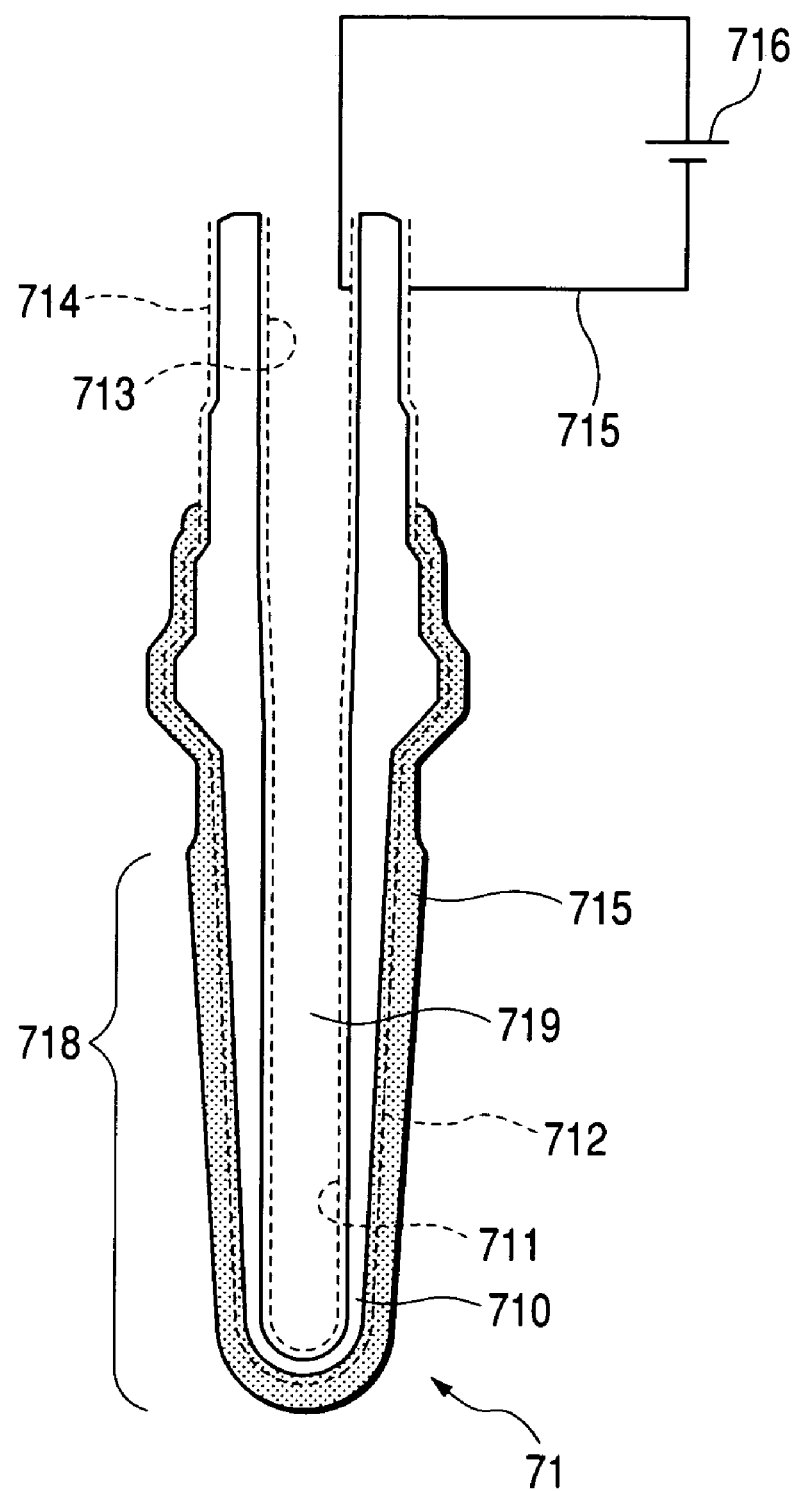
FIG. 18 is an enlarged longitudinal sectional view which shows the gas sensor element of FIG. 17.

The gas sensor element 71 includes, as shown in FIG. 18, a cup-shaped solid electrolyte body 710 which defines therein an air chamber 719 into which the air is admitted from outside the gas sensor 7. An inner electrode 711 is formed on an inner wall of the solid electrolyte body 710 which is exposed to the air chamber 719. The inner electrode 711 extends to a lead 714 formed on an upper inner wall of the solid electrolyte body 710. An outer electrode 712 is formed on an outer wall of the solid electrolyte body 710 which communicates electrically with a lead 714 formed on an upper outer wall of the solid electrolyte body 710. The outer electrode 712 and the lead 714 are covered with a porous protective layer (or a diffusion resistance layer) 715.

The gas sensor element 71 has an electrochemical cell 718 installed within the measurement gas cover assembly 701. The electrochemical cell 718 is made up of the electrodes 711 and 712 and the solid electrolyte body 710. The gas sensor element 71 is responsive to voltage applied to the electrodes 711 and 712 through the leads 713 and 714 to produce an electromotive force.

The aging treatment is accomplished, like the first embodiment, by connecting a control circuit 715 equipped with a power supply 715 to the inner and outer electrodes 711 and 712 through the leads 713 and 714 and applying the dc current thereto. This enhances the activation of the gas sensor element 71.

Figure 19:
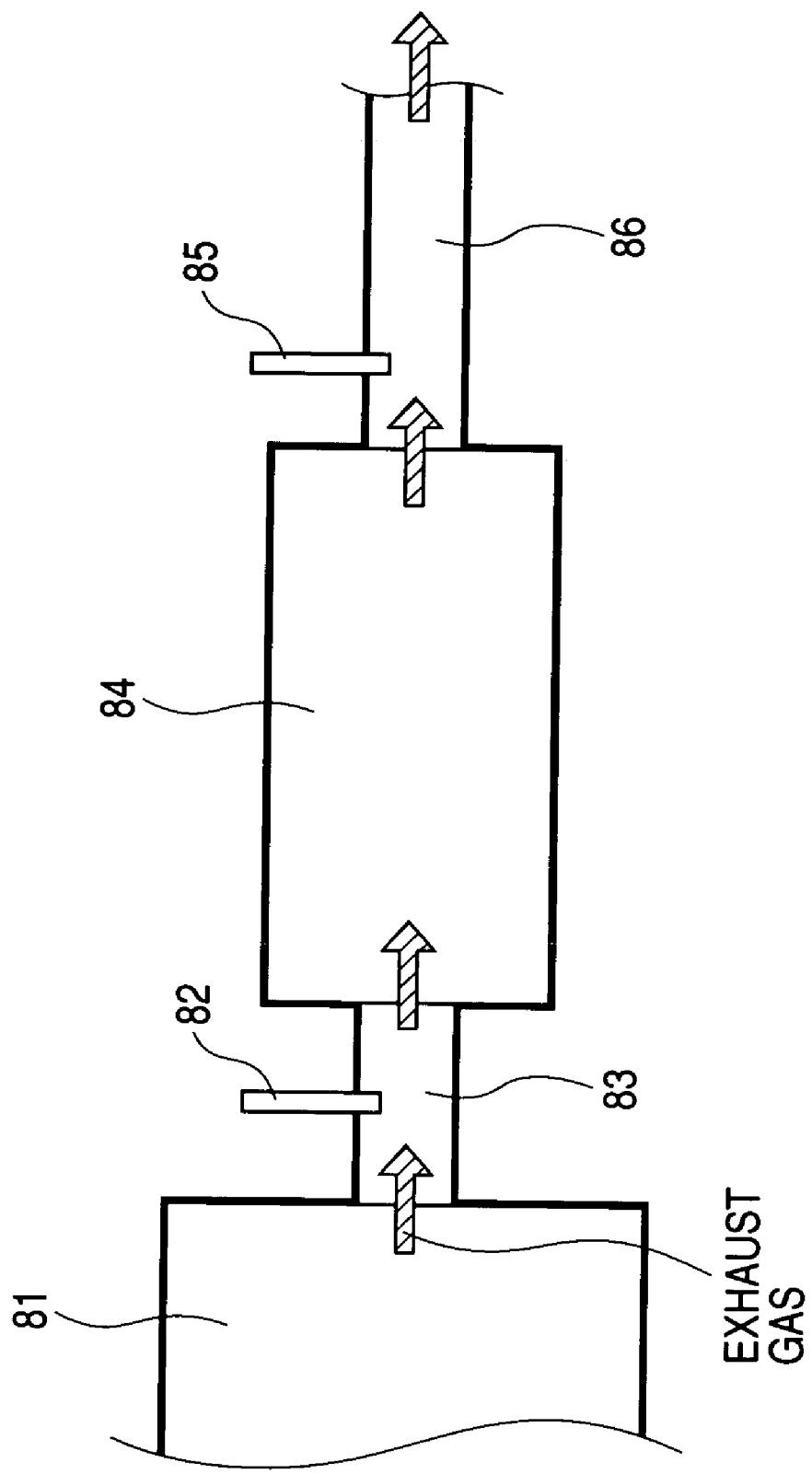
FIG. 19 is a view which shows a reconditioning system according to the twelfth embodiment of the invention which works to recondition gas sensor elements installed in an exhaust system of an automotive internal combustion engine.

FIG. 19 shows a twelfth embodiment of the invention in which an air-fuel ratio sensor 82 and a NOx sensor 85 installed in an exhaust system of an automotive vehicle are reconditioned by a reconditioning system.

The exhaust system has a catalytic converter 84 disposed between exhaust pipes 83 and 86. The exhaust pipe 83 is joined to a combustion chamber 81 of an internal combustion engine. The catalytic converter 84 has disposed therein a three-way catalyst which works to remove air pollutants such as NOx contained in exhaust gasses of the engine.

The three-way catalyst of the catalytic converter 81 exhibits a maximum efficiency of purification of emissions when the air-fuel ratio within the combustion chamber 81 is a stoichiometric air-fuel ratio. Therefore, the burning of an air-fuel mixture within the combustion chamber 81 is controlled based on the air-fuel ratio within the combustion chamber 81 determined as a function of the concentration of oxygen ($O_2$) within the exhaust gasses measured by the air-fuel ratio sensor 82 installed upstream of the catalytic converter 84.

The three-way catalyst of the catalytic converter 84 is usually deteriorated by the purification of emissions for a long period of time. The degree of such deterioration is determined by measuring the concentration of NOx contained within emissions of the engine through the NOx sensor 84 installed downstream of the catalytic converter 84. The three-way catalyst is reconditioned based on the NOx concentration.

The air-fuel ratio sensor 82 is equipped with any one of the gas sensor elements of the above embodiments designed to measure the concentration of oxygen ($O_2$). The NOx sensor 85 may be equipped with the gas sensor element 4 as illustrated in FIG. 14.

Usually, when the vehicle is parked, the temperature of the exhaust pipes 83 and 86 is substantially identical with an ambient temperature of the vehicle, while they reach approximately 1000° C. when the vehicle is running and emitting hot exhaust gasses. The gas sensor elements installed in the air-fuel ratio sensor 82 and the NOx sensor 85 are, thus, subjected to a thermal load cyclically within a range of –20° C. to 1000° C., which leads to a decrease in activation of the electrochemical cell.

The decrease in activation of the electrochemical cell results in an increase in the activation temperature of the gas sensor element. The reconditioning system of this embodiment, thus, works to apply the dc current to each of the air-fuel ratio sensor 82 and the NOx sensor 85 at a given voltage V cyclically during running of the vehicle to recondition the activation of the gas sensor element.

The reconditioning system may be provided by a control circuit designed to pick up an output of each of the air-fuel ratio sensor 82 and the NOx sensor 85 and apply the voltage thereto or an exclusive circuit. The reconditioning of the air-fuel ratio sensor 82 and the NOx sensor 85 is achieved preferably within an interval between measurements of the air-fuel ratio and the concentration of NOx.

The voltage V used in the aging treatment is, like the above embodiments, within a range of $V_2 \leq V \leq 2V_2$ where $V_2$ is a maximum voltage within a limiting current range of the electrochemical cell of each gas sensor element.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

The aging treatment in each of the first to eleventh embodiments may alternatively be performed after production or during use of the gas sensor element after installed in a gas sensor.

What is claimed is:

1. A gas sensor element comprising:
   at least one electrochemical cell including a solid electrolyte body made of a partially stabilized zirconia;
   a pair of electrodes disposed on said solid electrolyte body; and
   a discolored portion formed in said solid electrolyte body between said electrodes, said discolored portion having a color that differs from a color of a remainder of said solid electrolyte body;
   wherein if a value of a limiting current produced by said electrochemical cell at 700° C. in the air is defined as $I_{700}$, and a value of the limiting current at 900° C. in the air is defined as $I_{900}$, a relation of $0.8 \times I_{900} \leq I_{700} \leq 1.2 \times I_{900}$ is satisfied,
   wherein the discolored portion is formed by applying a dc current to the electrochemical cell through the electrodes,
   wherein the voltage V of the dc current is given by the relation $1.2\ V_2 \leq V \leq 1.5\ V_2$, where $V_2$ is a maximum voltage within a range where a limiting current is produced in the electrochemical cell, and
   wherein the discolored portion occupies 80% by volume of the portion of the solid electrolyte body sandwiched between said electrodes and through which oxygen ions pass.

2. A gas sensor element as set forth in claim 1, wherein the discolored portion has a conductivity higher than a conductivity of a remaining portion of the solid electrolyte body, whereby the discolored portion has a lower activation temperature than a remaining portion of the solid electrolyte body.

3. A gas sensor element as set forth in claim 2, wherein the discolored portion is formed by the reduction of the zirconia.

4. A gas sensor element as set forth in claim 1, formed as a laminate of a diffusion resistance layer, the solid electrolytic body, a spacer, and a ceramic heater, wherein the spacer has formed therein an air chamber into which air is admitted as a reference gas, and one of said electrodes is disposed between the spacer and the solid electrolytic body and works as a reference gas electrode, wherein the other of said electrodes is covered with the diffusion resistance layer and works as a measurement gas electrode, and wherein an insulating layer is disposed on the solid electrolytic body and has formed therein an opening defining a measurement gas chamber for a gas to be measured through which said other of said electrodes faces said solid electrolytic body.

5. A gas sensor element as set forth in claim 1, wherein said discolored portion is visually distinguishable by a human eye from the remainder of the solid electrolytic body.

6. A gas sensor element as set forth in claim 1, wherein the discolored portion is dark brown so as to be visually distinguishable by a human eye from the remainder of the solid electrolytic body which is gray or light brown in color as a whole.

7. A gas sensor element of claim 1, formed of a laminate of a porous protective layer, the solid electrolyte body, a spacer and a ceramic heater, one of said electrodes being exposed to an air chamber defined by the spacer and working as a reference gas electrode and the other electrode being covered with the porous protective layer exposed to a gas to be measured.

8. A gas sensor element of claim 1, further comprising a second electrochemical cell defined by a second solid electrolytic body and a second pair of electrodes, so that the gas sensor element has a two cell structure made of a laminate of a porous protective layer, said first and second solid electrolyte bodies, first and second spacers and a ceramic heater, and wherein said first and second electrolyte bodies are discolored between said respective pairs of electrodes to decrease the activation temperature of the first and second electrochemical cells.

9. A gas sensor element as set forth in claim 8, wherein dc current is applied to the electrodes of the first electrochemical cell and to the electrodes of the second electrochemical cell.

10. A gas sensor element comprising:
    at least one electrochemical cell including a solid electrolyte body made of a partially stabilized zirconia;
    a pair of electrodes disposed on said solid electrolyte body; and
    a discolored portion formed in said solid electrolyte body between said electrodes, said discolored portion having a color that differs from a color of a remainder of said solid electrolyte body;
    wherein the discolored portion is formed by applying a dc current to the electrochemical cell through the electrodes,
    wherein the voltage V of the dc current is given by the relation $1.2\ V_2 \leq V \leq 1.5\ V_2$, where $V_2$ is a maximum voltage within a range where a limiting current is produced in the electrochemical cell, and
    wherein the discolored portion occupies 80% by volume of the portion of the solid electrolyte body sandwiched between said electrodes and through which oxygen ions pass, and
    wherein said solid electrolyte body is discolored between said pair of electrodes to decrease the activation temperature of the electrochemical cell.

11. A gas sensor element as set forth in claim 10, wherein the discolored portion is dark brown so as to be visually distinguishable from the remainder of the solid electrolytic body which is gray or light brown in color as a whole.

12. A gas sensor element of claim 10, formed of a laminate of a porous protective layer, the solid electrolyte body, a spacer and a ceramic heater, one of said electrodes being exposed to an air chamber defined by the spacer and working as a reference gas electrode and the other electrode being covered with the porous protective layer exposed to a gas to be measured.

13. A gas sensor element of claim 10, further comprising a second electrochemical cell defined by a second solid electrolytic body and a second pair of electrodes, so that the gas sensor element has a two cell structure made of a laminate of a porous protective layer, said first and second solid electrolyte bodies, first and second spacers and a ceramic heater, and wherein said first and second electrolyte bodies are discolored between said respective pairs of electrodes to decrease the activation temperature of the first and second electrochemical cells.

* * * * *